(12) United States Patent
Kierce

(10) Patent No.: US 6,428,503 B1
(45) Date of Patent: Aug. 6, 2002

(54) SURGICAL INSTRUMENT FOR PROVIDING SUCTION AND IRRIGATION

(75) Inventor: Paul C. Kierce, Hull, MA (US)

(73) Assignee: ATC Technologies, Inc., Woburn, MA (US)

(*) Notice: Subject to any disclaimer, the term of this patent is extended or adjusted under 35 U.S.C. 154(b) by 0 days.

(21) Appl. No.: 09/484,939

(22) Filed: Jan. 18, 2000

Related U.S. Application Data

(60) Provisional application No. 60/116,537, filed on Jan. 19, 1999.

(51) Int. Cl.[7] ................................. A61M 3/00
(52) U.S. Cl. .......................... 604/43; 606/41
(58) Field of Search .................. 604/43, 27, 280, 604/35; 606/41, 45, 46, 170, 49, 50

(56) References Cited

U.S. PATENT DOCUMENTS

| | | | | |
|---|---|---|---|---|
| 2,008,526 A | | 7/1935 | Wappler et al. | 174/89 |
| 2,442,966 A | | 6/1948 | Wallace | 128/303.15 |
| 3,902,494 A | | 9/1975 | Haberlen et al. | 128/275.1 |
| 4,708,717 A | * | 11/1987 | Deane et al. | 604/35 |
| 5,085,658 A | | 2/1992 | Meyer | 606/46 |
| 5,190,541 A | | 3/1993 | Abele et al. | 606/46 |
| 5,221,281 A | | 6/1993 | Klicek | 606/45 |
| 5,261,905 A | | 11/1993 | Doresey, III | 606/45 |
| 5,267,994 A | | 12/1993 | Gentelia et al. | 606/15 |
| 5,290,282 A | | 3/1994 | Casscells | 606/29 |
| 5,300,069 A | | 4/1994 | Hunsberger et al. | 606/37 |
| 5,304,176 A | | 4/1994 | Phillips | 606/41 |
| 5,324,254 A | | 6/1994 | Phillips | 604/21 |
| 5,364,395 A | | 11/1994 | West, Jr. | 606/46 |
| 5,366,476 A | | 11/1994 | Noda | 606/206 |
| 5,397,333 A | * | 3/1995 | Knoepfler | 606/170 |
| 5,401,274 A | | 3/1995 | Kusunoki | 606/41 |
| 5,423,813 A | | 6/1995 | Kaiser et al. | 606/46 |
| 5,460,629 A | | 10/1995 | Shlain et al. | 606/46 |
| 5,501,654 A | | 3/1996 | Failla et al. | 600/204 |
| 5,562,640 A | * | 10/1996 | McCabe et al. | 604/280 |
| 5,637,110 A | * | 6/1997 | Pennybacker et al. | 606/46 |
| 5,662,647 A | * | 9/1997 | Crow et al. | 606/41 |
| 5,766,167 A | * | 6/1998 | Eggers et al. | 606/46 |
| 5,792,139 A | * | 8/1998 | Chambers et al. | 606/41 |
| 5,830,214 A | | 11/1998 | Flom et al. | 606/41 |
| 5,902,264 A | * | 5/1999 | Toso et al. | 604/27 |
| 6,293,945 B1 | * | 9/2001 | Parins et al. | 606/45 |

* cited by examiner

Primary Examiner—Teresa Walberg
Assistant Examiner—Leonid M Fastovsky
(74) Attorney, Agent, or Firm—Devine, Millimet & Branch, P.A.; Kevin J. Carroll; Paul C. Remus

(57) ABSTRACT

A surgical instrument for providing suction and/or irrigation has a surgical tool or electrode tip mounted within the wall of an elongated housing or cannula such that the passageway through the housing is substantially unobstructed. A mounting notch is formed in the elongated housing and the surgical tool is formed with a mounting tab that matches the mounting notch. The mounting tab is positioned into the mounting notch and is substantially flush with the wall of the elongated housing. The mounting tab is then secured to the wall of the elongated housing, for example, by laser welding. The surgical tool can be formed with various different tip shapes including, but not limited to, a J hook, an L hook, a spatula, a needle, and a ball. In one example, the surgical instrument is used as a laparoscopic electrosurgical instrument and the elongated housing and surgical tool are made of electrically conductive materials.

20 Claims, 7 Drawing Sheets

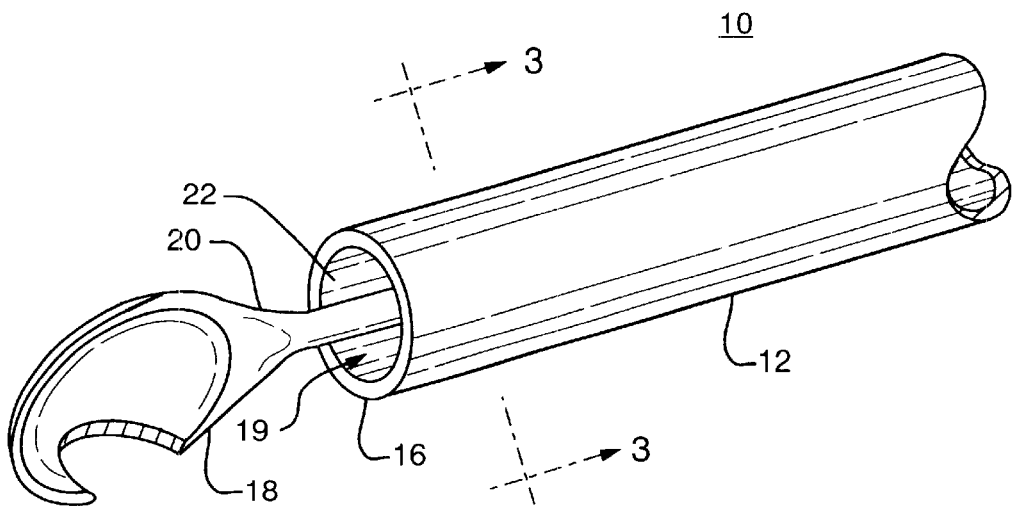
FIG. 1
(PRIOR ART)
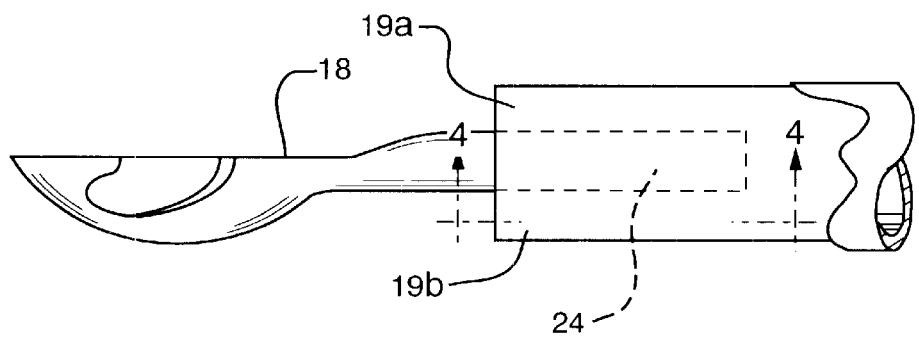
FIG. 2
(PRIOR ART)
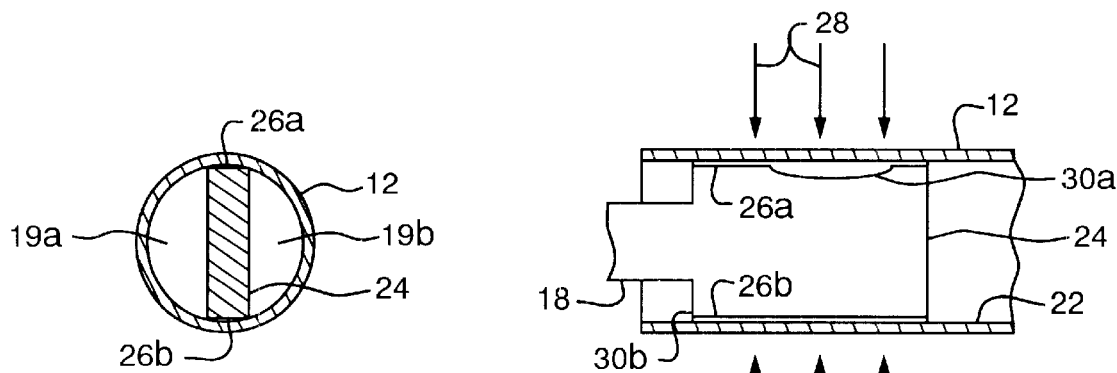
FIG. 3
(PRIOR ART)
FIG. 4
(PRIOR ART)

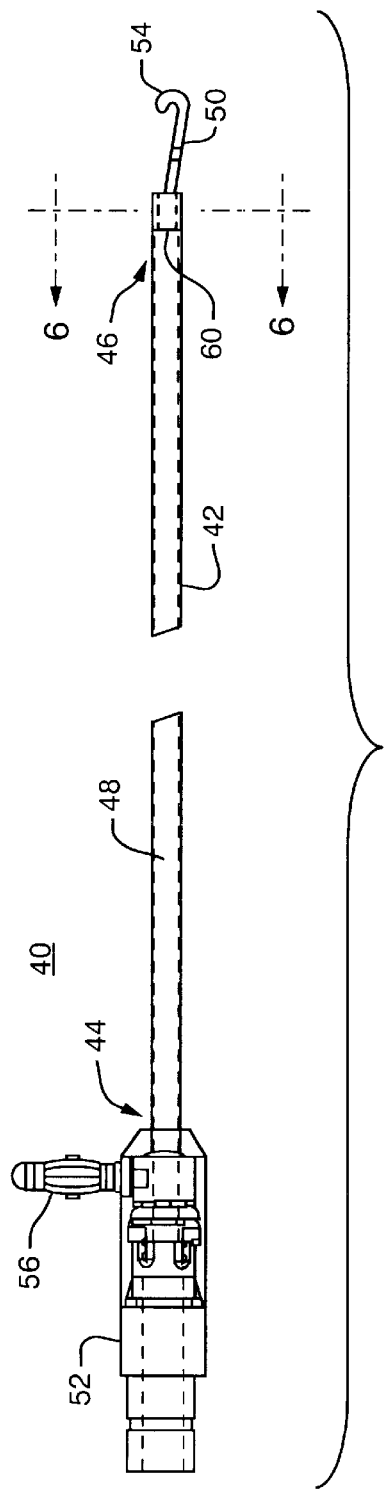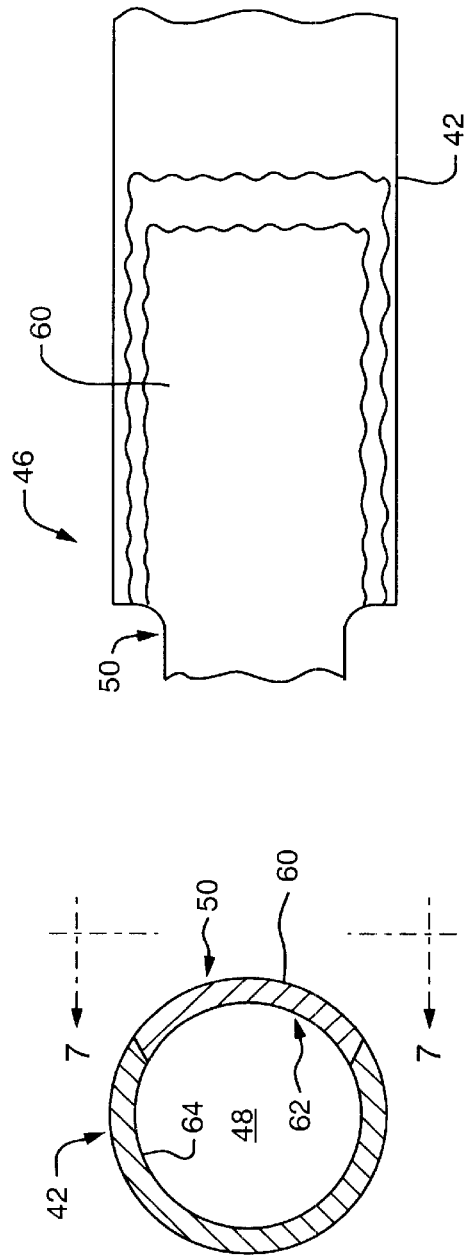

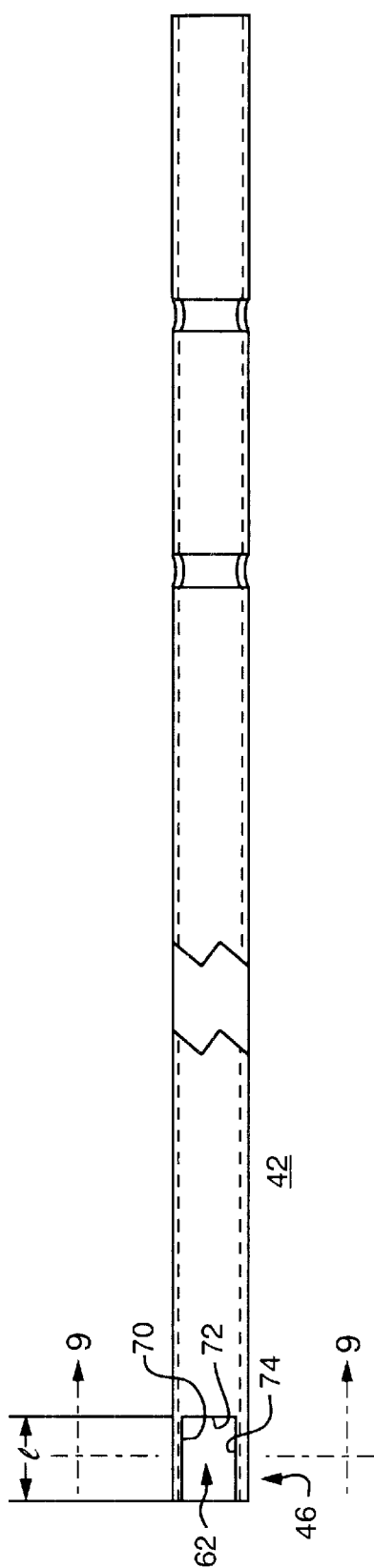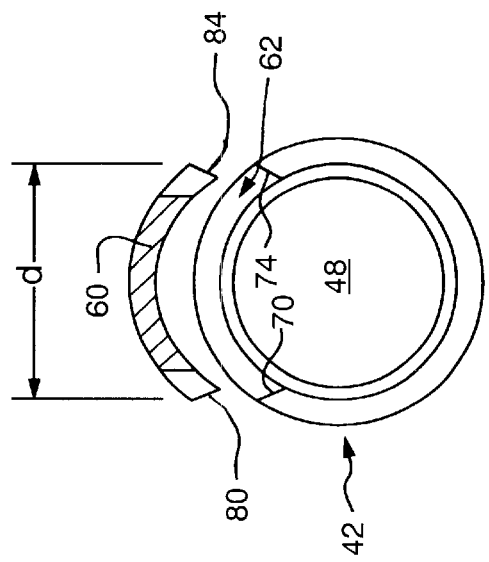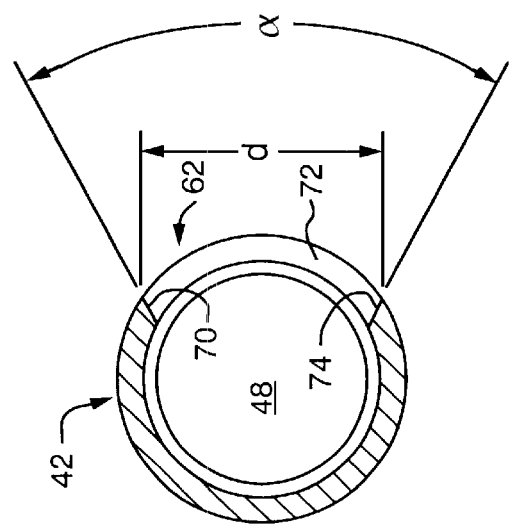

SURGICAL INSTRUMENT FOR PROVIDING SUCTION AND IRRIGATION

RELATED APPLICATIONS

This application claims the benefit of U.S. Provisional Patent Application Serial No. 60/116,537 filed Jan. 19, 1999, fully incorporated herein by reference.

FIELD OF THE INVENTION

The present invention relates to surgical instruments and in particular, to an electrosurgical laparoscopic instrument that provides suction and irrigation.

BACKGROUND

Surgical instruments are available that provide irrigation fluid and suction force to irrigate and evacuate the tissue at a surgical site or area where a surgical procedure is being performed. One example of such an instrument is an electrosurgical laparoscopic instrument 10, FIG. 1, which comprises a housing enclosure (or cannula) 12 having a distal end 16 and an electrode 18 extending from the distal end 16. The housing 12 forms a lumen or passageway 19 and is typically constructed of stainless steel with a Teflon shrink wrap insulation. The electrode 18 includes an insulated electrode connector 20 that extends into the stainless steel tube housing 12 and is attached to a portion of the inner surface 22 of the housing 12. In use, the laparoscopic instrument 10 is passed through a trocar.

According to one application of this instrument 10, the tip of the electrode 18 is used to dissect a gallbladder from the liver. Energy is applied through the surgical instrument 10 to the electrode 18 to assist in coagulation and cauterization during this dissection procedure. The passageway 19 allows for suction/irrigation of fluids through the housing 12, which is controlled, for example, by a trumpet valve. This type of electrosurgical laparoscopic instrument is described in greater detail in U.S. Pat. No. 5,261,905, incorporated herein by reference.

One problem with this type of electrosurgical laparoscopic instrument 10 as well as other surgical instruments that provide suction/irrigation is that the passageway 19 is obstructed by the electrode 18 or other surgical tool disposed at the distal end 16 of the instrument 10. In the electrosurgical laparoscopic instrument 10, the electrode 18 includes a mounting portion 24 mounted within the passageway 19, for example, by welding to the inner surface 22. The mounting of the electrode 18 thus obstructs the passageway 19 and results in separate flow regions 19a, 19b, FIGS. 2 and 3, on either side of the mounting portion 24 of the electrode 18. As a result, the surgical instrument is unable to provide full flow of irrigating fluid during irrigation and does not provide a full passageway for suction of fluid and tissues.

Another drawback of mounting the electrode 18 or other type of tool to the inner surface 22 within the passageway 19 of the housing 12 is the difficulty involved in cleaning the instrument. Tissue and other debris will often become lodged against the mounting portion 24 of the electrode 18 or other tool located within the passageway 19. Proper cleaning of surgical instruments is important to allow the instruments to be reused safely. The rigid tools commonly used to free debris and clear the passageways within the instruments often cause damage to the instruments. For example, the insulation around the housing 12 may break or become damaged, resulting in an unsafe electrosurgical instrument that cannot be reused or repaired.

A further drawback of the obstructed passageway is the inability to pass other surgical devices, such as, for example, a biopsy needle, through the passageway 19 at the distal end 16 of the surgical instrument 10 with the housing 12 acting as a guide. This capability would allow other surgical procedures, such as a biopsy procedure, to be performed at the surgical site more easily and less invasively without having to remove the instrument 10.

One attempt at solving this problem might be to weld the electrode 18 or tool to the outside of the housing 12. However, this increases the diameter unevenly and creates two outside diameters (ODs) on the cannula or housing 12, making it difficult to pass the cannula or housing 12 through a trocar. Further, the trocar typically includes a silicone seal that should fit snugly around the cannula to prevent site leakage. If the electrode 18 is welded to the outer surface of the cannula or housing 12, the electrode 18 might damage the seal or prevent the seal from fitting snug around the smaller OD of the cannula. A channel or dimple can be formed in the housing 12 to receive the electrode 18 and make the OD consistent, but this will affect the inside diameter (ID) and cause a partial obstruction within the passageway.

A further disadvantage of this electrosurgical laparoscopic instrument 10 and other such surgical instruments is the attachment between the electrode 18 and the inner surface 22 of the housing 12. One way of attaching the electrode 18, FIG. 4, to the inner surface 22 of the housing 12 is by laser welding the edges 26a, 26b of the mounting portion 24 by applying the laser generally in the direction of arrows 28. The laser welding, however, only welds the portions of the edges 26a, 26b that touch the inner surface 22 of the housing 12. If the edges 26a, 26b have any irregularities such as a non-linear edge 30a or a burr 30b caused, for example, by stamping the electrode 18, the edges 26a, 26b may have insufficient contact with the inner surface and may not be adequately welded. Thus, welding the electrode 18 to the inner surface 22 of the housing 12 can result in a weak attachment, possibly causing the electrode 18 to fall out, for example, during cleaning. The same problem with the strength/durability of the attachment occurs when the electrode is welded or otherwise secured to the outside surface of the housing 12.

A further problem occurs as a result of the passage of electrical current through an electrode 18 that is welded to the inside or outside surface of the housing 12. The gaps that form between the electrode 18 and the housing 12 may cause arcing or capacitive coupling to other insulated uninsulated areas.

Some electrosurgical instruments have the electrode formed integrally with the housing. In these instruments, however, certain tip shapes and geometries are not possible, such as a ball-shaped tip that has a diameter larger than the wall of the cannula.

Accordingly, a surgical instrument is needed that provides full flow irrigation and suction, that can be properly cleaned without damaging the instrument and safely reused, and that allows passage of another instrument or pharmaceuticals through the passageway. In particular, a need exists for an electrosurgical instrument having an electrode that is mounted as part of the wall of the housing to provide a substantially unobstructed passageway, to provide a stronger attachment between the electrode and the housing, to improve electrical contact, and to provide a number of different tip shapes.

SUMMARY OF THE INVENTION

The present invention features a surgical instrument comprising an elongated housing having a proximal end, a distal end, and a wall defining an inner lumen or passageway extending from the proximal end to the distal end. The surgical instrument further comprises a surgical tool extending from the wall of the elongated housing at the distal end such that the lumen or passageway is substantially unobstructed at the distal end. The tip of the surgical tool can have numerous different shapes including, but not limited to, a J hook, and an L hook, a spatula, a needle, and a ball. In one example, the surgical tool is bent such that the tip is positioned generally in the flow path extending from the passageway.

According to the preferred embodiment, the wall of the housing includes a mounting notch at the distal end and the surgical tool includes a mounting tab that mounts within the mounting notch, for example, by laser welding outer edges of the mounting tab to inner edges of the mounting notch. The inner edges of the mounting notch and the outer edges of the mounting tab are preferably angled to substantially match. In one embodiment, the mounting notch is generally rectangular shaped. In another embodiment, the mounting notch is generally key-shaped.

According to one embodiment, the surgical instrument is an electrosurgical instrument, such as an electrosurgical laparoscopic instrument, and the surgical tool acts as an electrode. In this embodiment, the elongated housing is made of an electrically conductive material and an insulating material is disposed around the elongated housing. The surgical tool is also made of an electrically conductive material and includes an insulating material disposed around a base portion of the tool leaving the tip of the electrode exposed.

The present invention also features a method of making a surgical instrument. The method generally comprises the steps of: forming an elongated housing having proximal end, a distal end, a wall defining an inner lumen extending from the proximal end to the distal end; forming a mounting notch in the wall at the distal end of the elongated housing; forming a surgical tool having a mounting tab and a tip extending from the mounting tab; inserting the mounting tab of the surgical tool in the mounting notch in the elongated housing; and securing the mounting tab to the wall of the elongated housing and within the mounting notch.

DESCRIPTION OF THE DRAWINGS

FIG. 1 is a perspective of an electrosurgical laparoscopic instrument according to the prior art;

FIG. 2 is a side view of the electrosurgical laparoscopic instrument according to the prior art;

FIG. 3 is a cross-sectional view of the instrument, according to the prior art, taken along line 3—3 in FIG. 1;

FIG. 4 is a cross-sectional view of the instrument, according to the prior art, taken along line 4—4 in FIG. 2;

FIG. 5 is a side view of a surgical instrument, according to the present invention;

FIG. 6 is a cross-sectional view of the surgical instrument, according to the present invention, taken along line 6—6 in FIG. 5;

FIG. 7 is a cross-sectional view of the surgical instrument, according to the present invention, taken along line 7—7 in FIG. 6;

FIG. 8 is a side view of a housing used in the surgical instrument, according to the present invention;

FIG. 9 is a cross-sectional view of the distal end of the housing, according to the present invention, taken along line 9—9 in FIG. 8;

FIG. 10 is an end view of the distal end of the housing and the mounting tab of the surgical tool aligned with the mounting notch in the housing, according to the present invention;

DESCRIPTION OF THE INVENTION

Figure 11A:
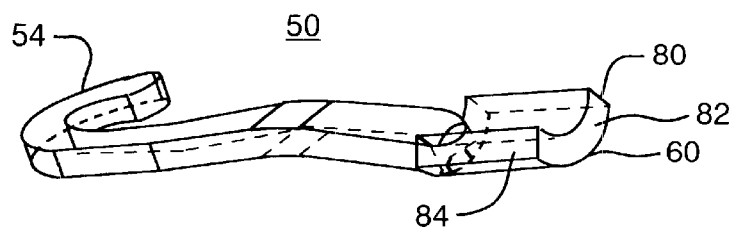
FIGS. 11A–11D are views of a surgical tool having a tip with a J-hook shape, according to one embodiment of the present invention.
Figure 11B:
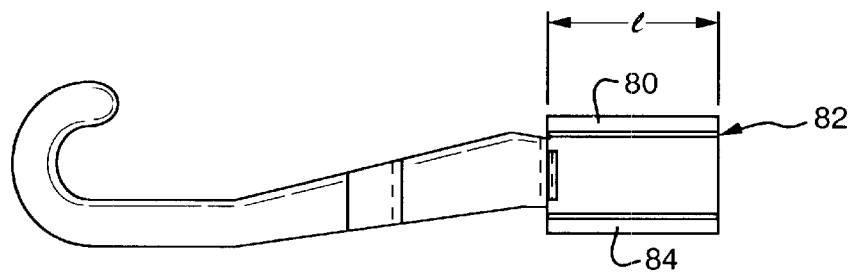

The surgical instrument 40, FIG. 5, according to the present invention, includes an elongated housing 42 having a proximal end 44, a distal end 46, and a lumen or passageway 48 extending through the housing 42 from the proximal end 44 to the distal end 46. The surgical instrument 40 also includes a surgical tool 50 extending from the elongated housing 42 at the distal end 46 and a base 52 attached to the housing 42 at the proximal end 44. The surgical tool 50 is attached to the housing 42 such that the passageway 48 at the distal end 46 of the housing 42 is substantially unobstructed, as will be described in greater detail below. The surgical tool 50 includes a tip 54 that performs surgical procedures at the surgical site within the patient, for example, by cutting and/or cauterizing tissue. The base 52 is adapted to be coupled to a control valve which controls the flow of fluid and/or tissue through the passageway 48 during irrigation or suction.

In one embodiment, the surgical instrument 40 is an electrosurgical instrument used for coagulating fluids and cauterizing tissues at the surgical site. In this embodiment, the housing 42 (also known as a cannula) and the surgical tool 50 (also known as an electrode tip) are made of an electrically-conductive material, such as stainless steel. The base 52 includes a conductor 56 for connecting to an external energy source to provide electric current through the housing 42 to the tip 54 of the surgical tool 50, which acts as an electrode to coagulate and cauterize. In this embodiment, a layer of insulating material, such as a TEFLON shrink wrap insulation, is disposed around the housing 42 and around a portion of the surgical tool 50 such that only a portion of the tip 54 becomes hot. Although the exemplary embodiment is an electrosurgical instrument, the concepts of the present invention can be applied to any type of surgical instrument.

According to the preferred embodiment, the surgical tool 50, FIGS. 6 and 7, includes a mounting tab 60 mounted within a mounting notch 62 formed within the side wall 64 of the housing 42 at the distal end 46. In one example, the mounting tab 60 is laser welded to the side wall 64 of the housing 42. The present invention also contemplates attaching or mounting the mounting tab 60 by soldering, brazing or any other method of attachment. By securing the mounting tab 60 of the surgical tool 50 within the mounting notch 62, the inner diameter (ID) within the housing 42 is substantially uniform and substantially without any obstructions. The unobstructed passageway 48 allows full flow of irrigation and full portability for suction of debris. Debris is also less likely to become lodged or clot the end of the passageway 48, allowing a simple cannula brush to pass through the passageway 48 for cleaning without damaging the instrument. The unobstructed passageway 48 also allows passage of other instruments (e.g., a biopsy needle) or wound management items (e.g., anti-clot gauze) and/or the delivery of pharmaceuticals.

Attaching the mounting tab 60 within the mounting notch 62 of the housing 42 also provides a substantially uniform outer diameter (OD) such that the requisite amount of energy will travel through the surgical tool 50 for coagulating and cauterizing. The instrument 40 can therefore be passed through a trocar without damaging the silicone seal.

According to the preferred embodiment, the mounting notch 62, FIGS. 8 and 9, has inner edges 70, 72, 74. The mounting notch 62 is preferably formed by making a generally pie-shaped cut through the housing 42 (FIG. 9) such that the side inner edges 70, 74 taper inwardly toward the passageway 48. The mounting tab 60, FIG. 10, on the surgical tool 50 includes side outer edges 80, 84 having a taper that matches the side inner edges 70, 74 within the mounting notch 62. In one example, the side inner edges 70, 74 within the notch 62 form an angle α of about 56° and the side outer edges 80, 84 of the tab 60 form an angle α of about 56° to match the side inner edges 70, 74. The distance d between the side inner edges 70, 74 of the notch 62 also preferably matches the distance d between the side outer edges 80, 84 of the tab 60. In the example shown, the distance d is about 0.135 in. The length l of the notch 62 and tab 60 also preferably matches and is about 0.190 in. in the exemplary embodiment. The tab 60 is preferably dimensioned to fit in the notch 62 such that the inside and outside surfaces of the cannula remain substantially round and concentric within commercially acceptable tolerances or standards.

Thus, when the mounting tab 60 is positioned within the mounting notch 62 the outer edges 80, 82, 84 are easily aligned with and contact the inner edges 70, 72, 74 of the mounting notch 62 with substantially 100% surface contact. The tapering of the inner edges 70, 72, 74 and outer edges 80, 82, 84 therefore increases the surface area that is in contact and improves the strength of the welded attachment. The close fit of the tab 60 within the notch 62 also creates a closed loop circuit with no break in current or gaps that cause arcing or current jumping when used as an electrosurgical instrument.

Figure 12:
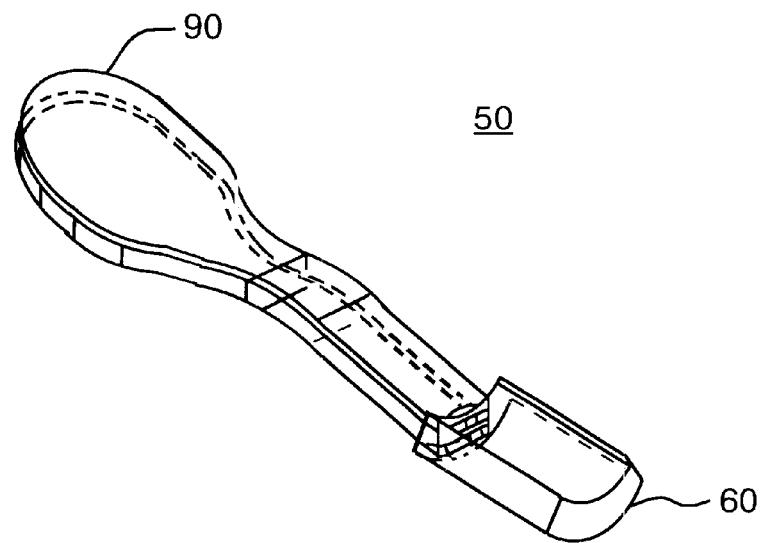
FIG. 12 is a perspective view of a surgical tool having a tip with a spatula shape, according to another embodiment of the present invention.
Figure 13:
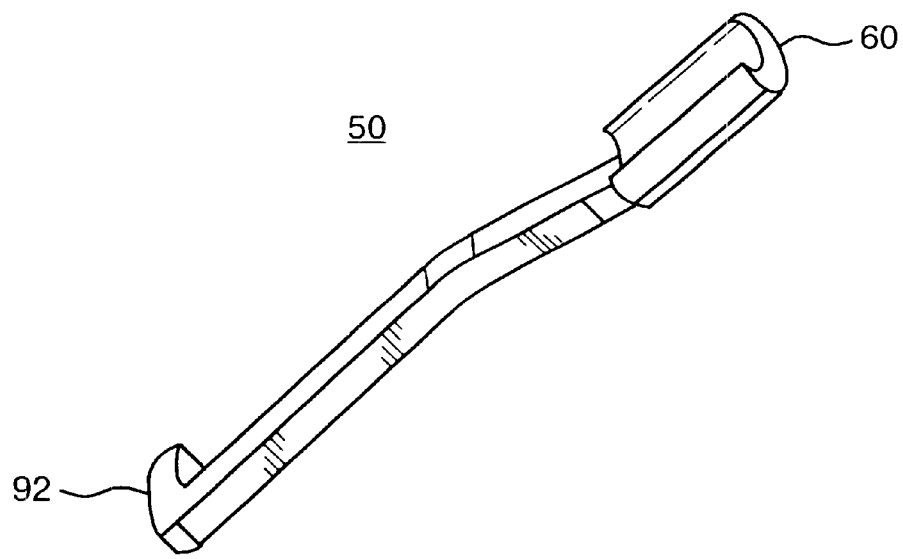
FIG. 13 is a perspective view of a surgical tool having a tip with an L-shape, according to a further embodiment of the present invention.
Figure 14:
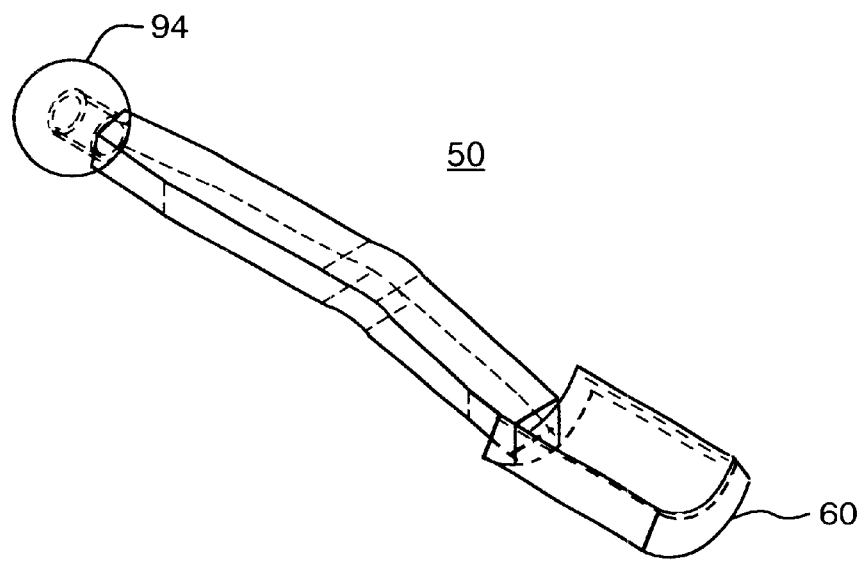
FIG. 14 is a perspective view of the surgical tool having a tip with a ball-shape, according to a further embodiment of the present invention.
Figure 15:
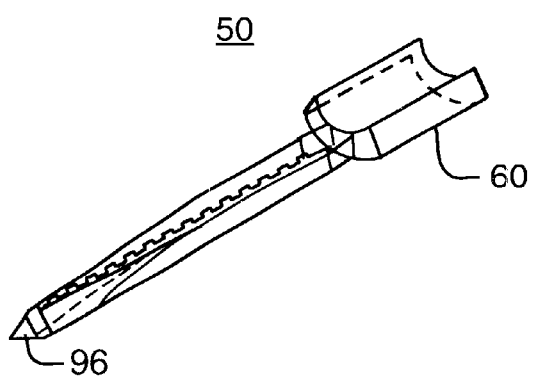
FIG. 15 is a perspective view of a surgical tool having a tip with a needle shape, according to a further embodiment of the present invention.

One advantage of the separately manufactured electrode tip or surgical tool 50 that fits into the side wall of the cannula or housing 42 is the ability to use different shaped tips. According to one embodiment, the surgical tool 50, FIGS. 11A–11D, has a tip 54 with a J-hook shape. According to another embodiment, the surgical tool 50, FIG. 12, includes a tip 90 having a spatula shape. According to a further embodiment, the surgical tool 50, FIG. 13, includes a tip 92 having a L-hook shape. According to a further embodiment, the surgical tool 50, FIG. 14, includes a tip 94 having a ball shape. According to a further embodiment, the surgical tool 50, FIG. 15, includes a tip 96 having a needle shape. In each of these embodiments, the mounting tab 60 is substantially the same. The housing 42 can thus be used with different surgical tools having tips of various shapes for use in various types of surgical procedures.

Figure 11C:
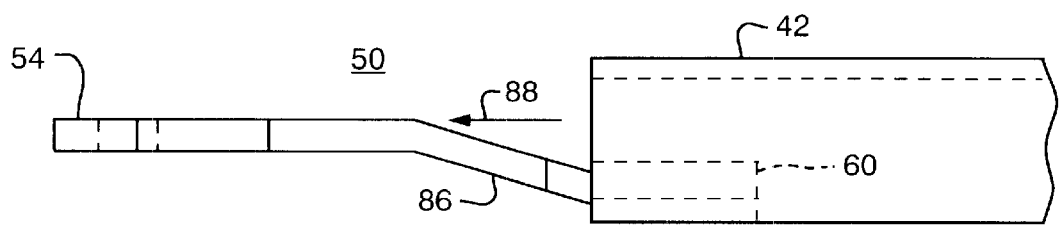
Figure 11D:
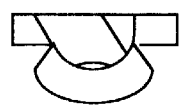

According to one embodiment, the surgical tool 50, FIG. 11C, includes a bend 86 such that the tip 54 lies generally in the flow path indicated generally by arrow 88. This construction facilitates flushing of the tip 54 of the surgical tool 50 even when the surgical tool 50 is secured to the housing 42 without obstructing the passageway 48. The surgeon has the ability to clear off the tip 54 during a procedure and can irrigate at the point of contact of a surgical site. From an ergonomic standpoint, the centering of the tip 54 allows the surgeon to more accurately pinpoint a surgical site. According to one example, the surgical tools 50 can be formed by conventional machining, such as milling or turning, by EDM machining, laser cutting, stamping, punch press, photo etch cutting, water jet cutting, metal injection molding, or any other process.

Figure 16:
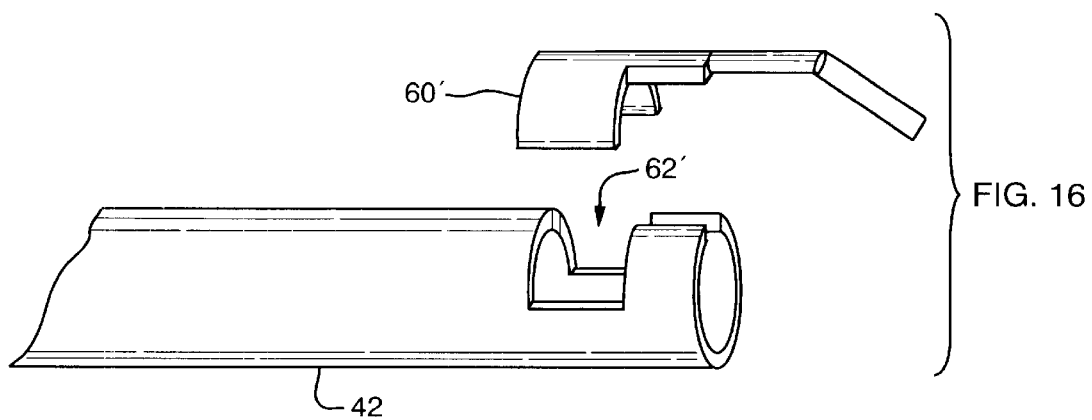
FIG. 16 is a side view of the distal end of a housing having a key-shaped mounting notch and matching key-shaped mounting tab, according to an alternative embodiment of the present invention.
Figure 17:
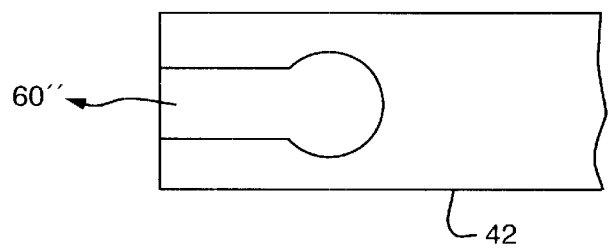
FIG. 17 is a side view of a key-shaped mounting notch, according to a further alternative embodiment.

According to another embodiment shown in FIG. 16, the mounting tab 60' and the mounting notch 62' have a matching key shape. This key-shaped construction facilitates assembly and further prevents the tab 60' from detaching from the housing 42. A mounting notch 62" having alternative key-shape is shown in FIG. 17.

Accordingly, the surgical instrument of the present invention includes surgical tools mounted to a distal end of a housing without significantly obstructing the inner diameter of the housing nor significantly increasing the outer diameter. The surgical instrument can therefore be more easily cleaned without damaging the instrument, provides improved suction/irrigation, and allows other surgical devices or material to be passed through the passageway within the housing. The manner in which the surgical tools are mounted to the housing according to the present invention also improves the strength of the surgical tool and the electrical conductivity through the electrode when used as an electrosurgical instrument.

Modifications and substitutions by one ordinary skill in the art are considered to be within the scope of the present invention.

What is claimed is:

1. A surgical instrument for use in suction/irrigation, said surgical instrument comprising:
    an elongated housing having a proximal end, a distal end, and a wall defining an inner lumen extending from said proximal end to said distal end, wherein said wall of said elongated housing includes a mounting notch at said distal end; and
    a surgical tool extending from said wall of said elongated housing at said distal end, wherein said surgical tool includes a tip and a mounting tab that mounts within said mounting notch such that said mounting tab is substantially flush with said wall.

2. The surgical instrument of claim 1 wherein inner edges of said mounting notch and outer edges of said mounting tab are angled to substantially match.

3. The surgical instrument of claim 2 wherein said outer edges of said mounting tab are laser welded to said inner edges of said mounting notch.

4. The surgical instrument of claim 1 wherein said mounting notch is generally rectangular shaped.

5. The surgical instrument of claim 1 wherein said mounting notch is generally key-shaped.

6. The surgical instrument of claim 1 wherein said surgical tool is bent such that said tip is positioned generally in the flow path extending from said lumen.

7. The surgical instrument of claim 1 wherein said tip of said surgical tool has a shape selected from the group consisting of a J hook, an L hook, a spatula, a needle, and a ball.

8. The surgical instrument of claim 1 wherein said elongated housing and said surgical tool are made of an electrically conductive material, wherein an insulating material is disposed around said elongated housing and a base of said surgical tool leaving said tip of said surgical tool exposed to act as an electrode.

9. The surgical instrument of claim 1 wherein an inner diameter and an outer diameter are substantially uniform at said distal end of said elongated housing.

10. A surgical tool for use with a surgical instrument, said surgical tool comprising:

a mounting tab for mounting in a matching notch in said surgical instrument;

a tip extending from said mounting tab, wherein said mounting tab and said tip are made of an electrically conductive material; and an insulating material disposed around a base of said tip.

11. The surgical tool of claim 10 wherein said tip has a shape selected from the group consisting of a J hook, an L hook, a spatula, a needle, and a ball.

12. The surgical tool of claim 10 wherein said mounting tab is key-shaped.

13. A method of making a surgical instrument comprising the steps of:

forming an elongated housing having a proximal end, a distal end, a wall defining an inner lumen extending from said proximal end to said distal end;

forming a mounting notch in said wall at said distal end of said elongated housing;

forming a surgical tool having a mounting tab and a tip extending from said mounting tab;

inserting said mounting tab of said surgical tool in said mounting notch in said elongated housing; and securing said mounting tab to said wall of said elongated housing and within said mounting notch.

14. The method of claim 13 wherein the step of forming said elongated housing includes machining said elongated housing, and wherein said step of forming said mounting notch includes removing a section of said wall at said distal end of said elongated housing.

15. The method of claim 13 wherein said step of forming said surgical tool includes metal injection molding.

16. The method of claim 13 wherein said step of securing said mounting tab to said wall of said elongated housing includes laser welding.

17. The method of claim 13 wherein said tip has a shape selected from the group consisting of a J hook, an L hook, a spatula, a needle, and a ball.

18. The method of claim 13 wherein said mounting tab is substantially flush with said wall of said elongated housing.

19. The method of claim 13 wherein said mounting notch and said mounting tab are formed having a matching key shape.

20. The method of claim 13 wherein said elongated housing and said surgical tool are made of an electrically conductive material, and further including the steps of:

covering said elongated housing with an insulating material; and covering a base of said surgical tool with an insulating material leaving said tip of said surgical tool exposed to act as an electrode.

* * * * *